US008891881B2

(12) United States Patent
Gupta et al.

(10) Patent No.: US 8,891,881 B2
(45) Date of Patent: Nov. 18, 2014

(54) SYSTEM AND METHOD FOR IDENTIFYING AN OPTIMAL IMAGE FRAME FOR ULTRASOUND IMAGING

(75) Inventors: Mithun Das Gupta, Bangalore (IN); Kajoli Banerjee Krishnan, Bangalore (IN); Pavan Kumar Veerabhadra Annangi, Bangalore (IN); Xiaoming Liu, Schenectady, NY (US); Sri Kaushik Pavani, Bangalore (IN); Navneeth Subramanian, Bangalore (IN); Jyotirmoy Banerjee, Bangalore (IN)

(73) Assignee: General Electric Company, Niskayuna, NY (US)

( * ) Notice: Subject to any disclaimer, the term of this patent is extended or adjusted under 35 U.S.C. 154(b) by 365 days.

(21) Appl. No.: 13/357,724

(22) Filed: Jan. 25, 2012

(65) Prior Publication Data
US 2013/0190600 A1 Jul. 25, 2013

(51) Int. Cl.
G06K 9/00 (2006.01)
G06K 9/62 (2006.01)

(52) U.S. Cl.
USPC .......................................... 382/209; 382/128

(58) Field of Classification Search
CPC .. A61B 8/0866; A61B 8/5215; A61B 8/5223; A61B 8/523
See application file for complete search history.

(56) References Cited

U.S. PATENT DOCUMENTS

| | | | |
|---|---|---|---|
| 5,579,768 A | 12/1996 | Klesenski | |
| 5,605,155 A | 2/1997 | Chalana et al. | |
| 6,012,458 A | 1/2000 | Mo et al. | |
| 6,056,691 A | 5/2000 | Urbano et al. | |
| 6,488,629 B1 | 12/2002 | Saetre et al. | |
| 7,672,491 B2* | 3/2010 | Krishnan et al. | 382/128 |
| 7,783,095 B2* | 8/2010 | Carneiro et al. | 382/128 |
| 7,806,824 B2 | 10/2010 | Ohtake | |
| 7,925,068 B2 | 4/2011 | Hoctor et al. | |
| 7,972,269 B2 | 7/2011 | Hayashi et al. | |
| 7,995,820 B2* | 8/2011 | de Barros Carneiro et al. | 382/128 |
| 8,411,950 B2* | 4/2013 | Akinyemi et al. | 382/173 |

(Continued)

FOREIGN PATENT DOCUMENTS

| | | |
|---|---|---|
| EP | 2293244 A1 | 3/2011 |
| EP | 2345992 A2 | 7/2011 |

OTHER PUBLICATIONS

Cohen et al., "Transabdominal three-dimensional volume imaging of the fetal brain at 18-24 weeks' gestation", International Journal of Gynecology & Obstetrics, 72 (2001), 145-150, 2001.*

(Continued)

Primary Examiner — Anand Bhatnagar
Assistant Examiner — Soo Park
(74) Attorney, Agent, or Firm — Seema S. Katragadda

(57) ABSTRACT

A method for identifying an optimal image frame is presented. The method includes receiving a selection of an anatomical region of interest in an object of interest. Furthermore, the method includes obtaining a plurality of image frames corresponding to the selected anatomical region of interest. The method also includes determining a real-time indicator corresponding to the plurality of acquired image frames, wherein the real-time indicator is representative of quality of an image frame. In addition, the method includes communicating the real-time indicator to aid in selecting an optimal image frame. Systems and non-transitory computer readable medium configured to perform the method for identifying an optimal image frame are also presented.

20 Claims, 11 Drawing Sheets

(56) References Cited

U.S. PATENT DOCUMENTS

| | | | |
|---|---|---|---|
| 8,699,823 B2* | 4/2014 | Boettger et al. | 382/294 |
| 2002/0102023 A1* | 8/2002 | Yamauchi | 382/199 |
| 2003/0065265 A1 | 4/2003 | Jackson et al. | |
| 2003/0114755 A1 | 6/2003 | Jong et al. | |
| 2004/0254439 A1 | 12/2004 | Fowkes et al. | |
| 2007/0066880 A1 | 3/2007 | Lee et al. | |
| 2008/0051659 A1 | 2/2008 | Waki et al. | |
| 2009/0005679 A1 | 1/2009 | Dala-Krishna et al. | |
| 2009/0074280 A1 | 3/2009 | Lu et al. | |
| 2009/0093717 A1 | 4/2009 | Carneiro et al. | |
| 2010/0125204 A1 | 5/2010 | Yoo et al. | |
| 2010/0217123 A1* | 8/2010 | Eran et al. | 600/437 |
| 2011/0144499 A1 | 6/2011 | Yoo et al. | |
| 2011/0152686 A1 | 6/2011 | Snook et al. | |
| 2011/0160588 A1 | 6/2011 | Ichikawa | |
| 2011/0170755 A1* | 7/2011 | Buelow et al. | 382/128 |
| 2011/0172536 A1* | 7/2011 | Do et al. | 600/443 |
| 2011/0196236 A1* | 8/2011 | Swamy et al. | 600/443 |
| 2011/0213250 A1* | 9/2011 | Vion et al. | 600/443 |
| 2011/0295120 A1* | 12/2011 | Lee | 600/443 |
| 2011/0319737 A1* | 12/2011 | Hill | 600/365 |
| 2013/0054270 A1* | 2/2013 | Sparks et al. | 705/3 |
| 2013/0158402 A1* | 6/2013 | Annangi et al. | 600/443 |
| 2013/0223716 A1* | 8/2013 | Mori et al. | 382/131 |

OTHER PUBLICATIONS

Hadlock et al., "Fetal head circumference: relation to menstrual age," American Journal of Roentgenology, 1982; 138: 649-653, 1982.*

Brekke et al.; "Dynamic 3D Ultrasound Imaging of the Fetal Heart"; 2002 IEEE Ultrasonics Symposium;vol. 2; pp. 1593-1596.

* cited by examiner

SYSTEM AND METHOD FOR IDENTIFYING AN OPTIMAL IMAGE FRAME FOR ULTRASOUND IMAGING

BACKGROUND

Embodiments of the present disclosure relate to imaging, and more particularly to the identification of an optimal image frame for ultrasound imaging.

As will be appreciated, ultrasound imaging has been employed for a wide variety of applications. During the process of ultrasound scanning, a clinician attempts to capture a view of a certain anatomy which confirms/negates a particular medical condition. Once the clinician is satisfied with the quality of the view or the scan plane, the image is frozen to proceed to the measurement phase. For example, ultrasound images are routinely used to assess gestational age (GA) and weight of a fetus or to monitor cardiac health of a patient. Ultrasound measurements of specific features of fetal anatomy such as the head, abdomen or the femur from two-dimensional (2D) or three-dimensional (3D) image data are used in the determination of GA, assessment of growth patterns and identification of anomalies. Similarly, for cardiac applications, thicknesses of cardiac walls are routinely measured by cardiologists to check for cardiomyopathy.

Image acquisition is quite a challenging problem for sonographers. Currently, image acquisition takes anywhere between 1 to 5 minutes for each correct scan plane acquisition and more so for novice clinicians. The other challenge the less experienced clinicians/sonographers face is the ability to correctly identify acceptable scan plane frames. It is also desirable for the clinicians to have an understanding of how far they are from correct scan plane. Moreover, ultrasound images are subject to both patient and operator/clinician variability. Also, determining a quality of an image frame is fraught with challenges. Particularly, pixel intensities in the images vary significantly with different gain settings.

Currently, there exist semi-automated and automated techniques for ultrasound image analysis. However, ultrasound images, such as fetal ultrasound images are invariably contaminated by a number of factors that can compromise a diagnosis. The contaminants may include factors, such as, but are not limited to, near field haze due to fat deposits, unpredictable patient movement, and the ubiquitous speckle noise. Operator variability also limits reproducibility of ultrasound imagery and measurement. There are multiple reasons for the inter-operator variability. Firstly, two-dimensional (2D) echocardiography visualizes only a cross-sectional slice of a three-dimensional structure, commonly referred to as the scan plane. Even small changes in positioning of the transducer, which has six degrees of freedom, may lead to significant changes in the scene visualized, which may in turn lead to incorrect measurement. In addition, sub-optimal ultrasound image settings such as gain, time-gain compensation may decrease the ability to visualize the internal structures of the human body.

Early efforts at improving robustness and accuracy of clinical workflow have tended to focus on semi-automated methods that include, for example, femur segmentation, head segmentation and cardiac segmentation. However, the above processes tend to be time-consuming. Additionally, use of these techniques may entail user intervention or call for a trained sonographer. These techniques may also be subject to operator variability or may be prone to false detection. In remote or rural markets it may be particularly difficult to obtain services of a trained ultrasonographer or ultrasound technician, causing remote regions to be poorly served or underserved.

BRIEF DESCRIPTION

In accordance with aspects of the present technique, a method for identifying an optimal image frame is presented. The method includes receiving a selection of an anatomical region of interest in an object of interest. Moreover, the method includes obtaining a plurality of image frames corresponding to the selected anatomical region of interest. The method also includes determining a real-time indicator corresponding to the plurality of acquired image frames, wherein the real-time indicator is representative of quality of an image frame. Additionally, the method includes communicating the real-time indicator to aid in selecting an optimal image frame. A non-transitory computer readable medium including one or more tangible media, where the one or more tangible media include code adapted to perform the method for identifying an optimal image frame is also presented.

In accordance with another aspect of the present technique, a system is presented. The system includes a rating platform configured to receive a selection of an anatomical region of interest in an object of interest, obtain a plurality of image frames corresponding to the selected anatomical region of interest, determine a real-time indicator corresponding to the plurality of acquired image frames, wherein the real-time indicator is representative of quality of an image frame, and communicate the real-time indicator to aid in selecting an optimal image frame.

In accordance with yet another aspect of the present technique, an imaging system is presented. The imaging system includes an acquisition subsystem configured to obtain a plurality of image frames corresponding to a region of interest in an object of interest. In addition, the imaging system includes a processing subsystem in operative association with the acquisition subsystem and including a rating platform, wherein the rating platform includes a feature extraction module configured to extract one or more features of interest from the plurality of image frames, a quality metric generator module configured to generate a quality metric corresponding to one or more image frames in the plurality of image frames, an image frame selector module configured to select one or more image frames based on the quality metric, and a feedback module configured to generate and communicate in real-time an indicator representative of the quality metric.

DRAWINGS

These and other features, aspects, and advantages of the present disclosure will become better understood when the following detailed description is read with reference to the accompanying drawings in which like characters represent like parts throughout the drawings, wherein.

Figure 1:
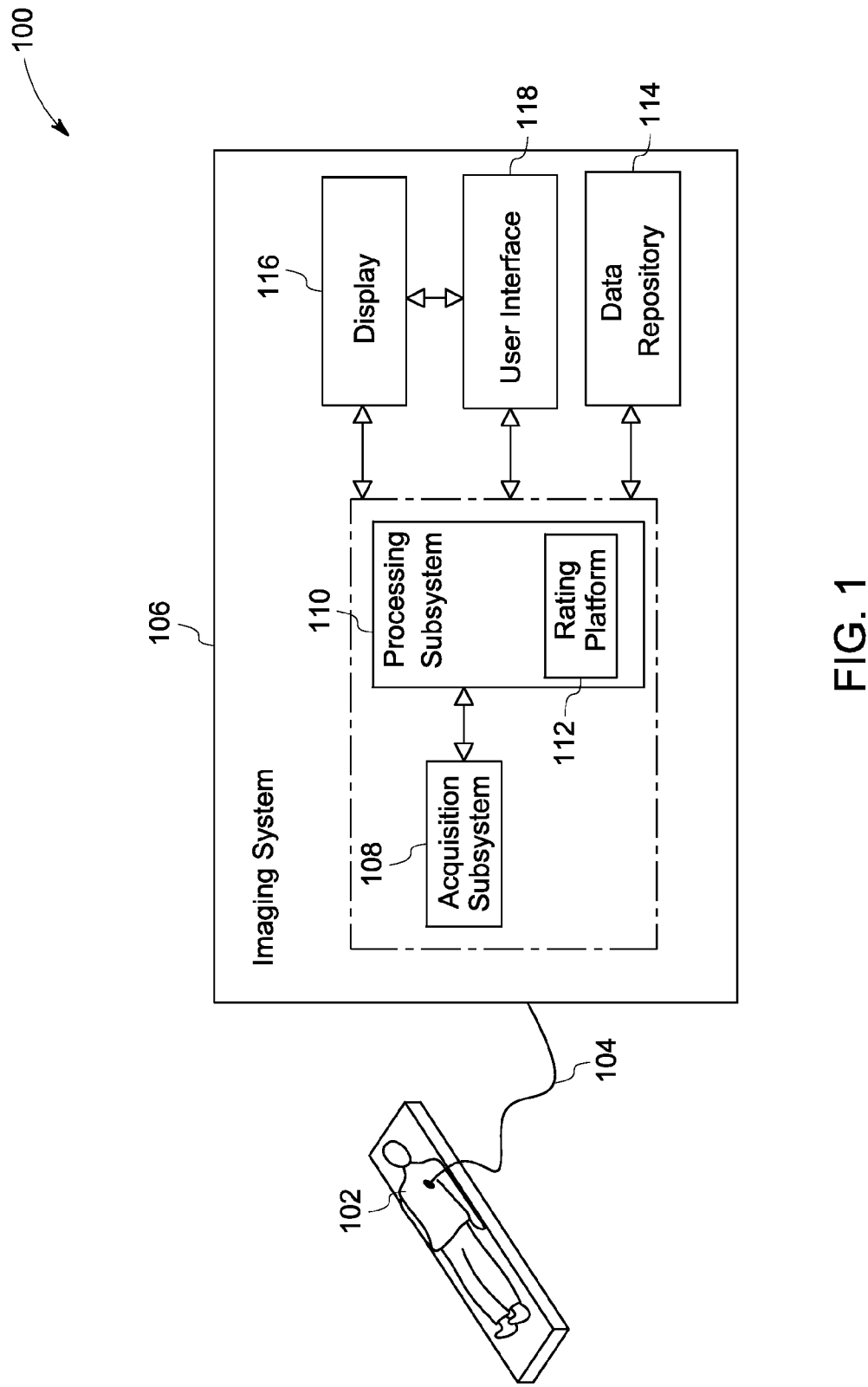
FIG. 1 is a diagrammatical illustration of a system for automated identification of an optimal image frame for ultrasound imaging, in accordance with aspects of the present technique.
Figures 6A, 6B:
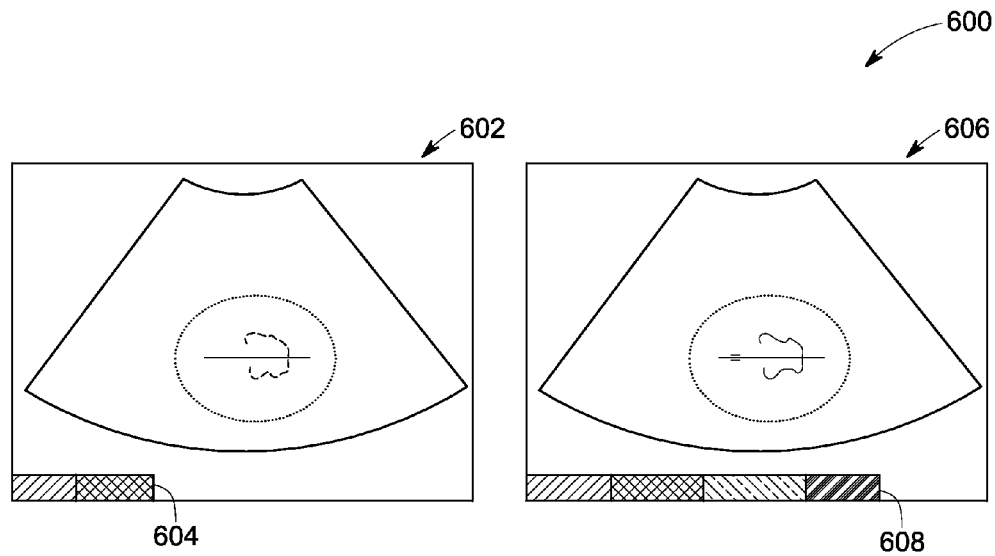
Figure 7:
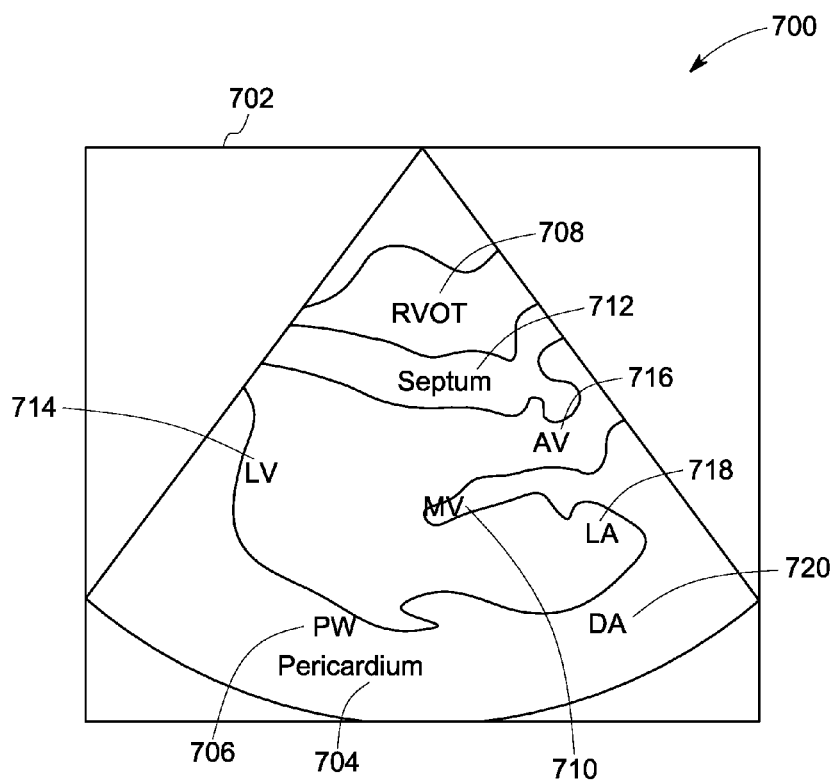
Figure 8:
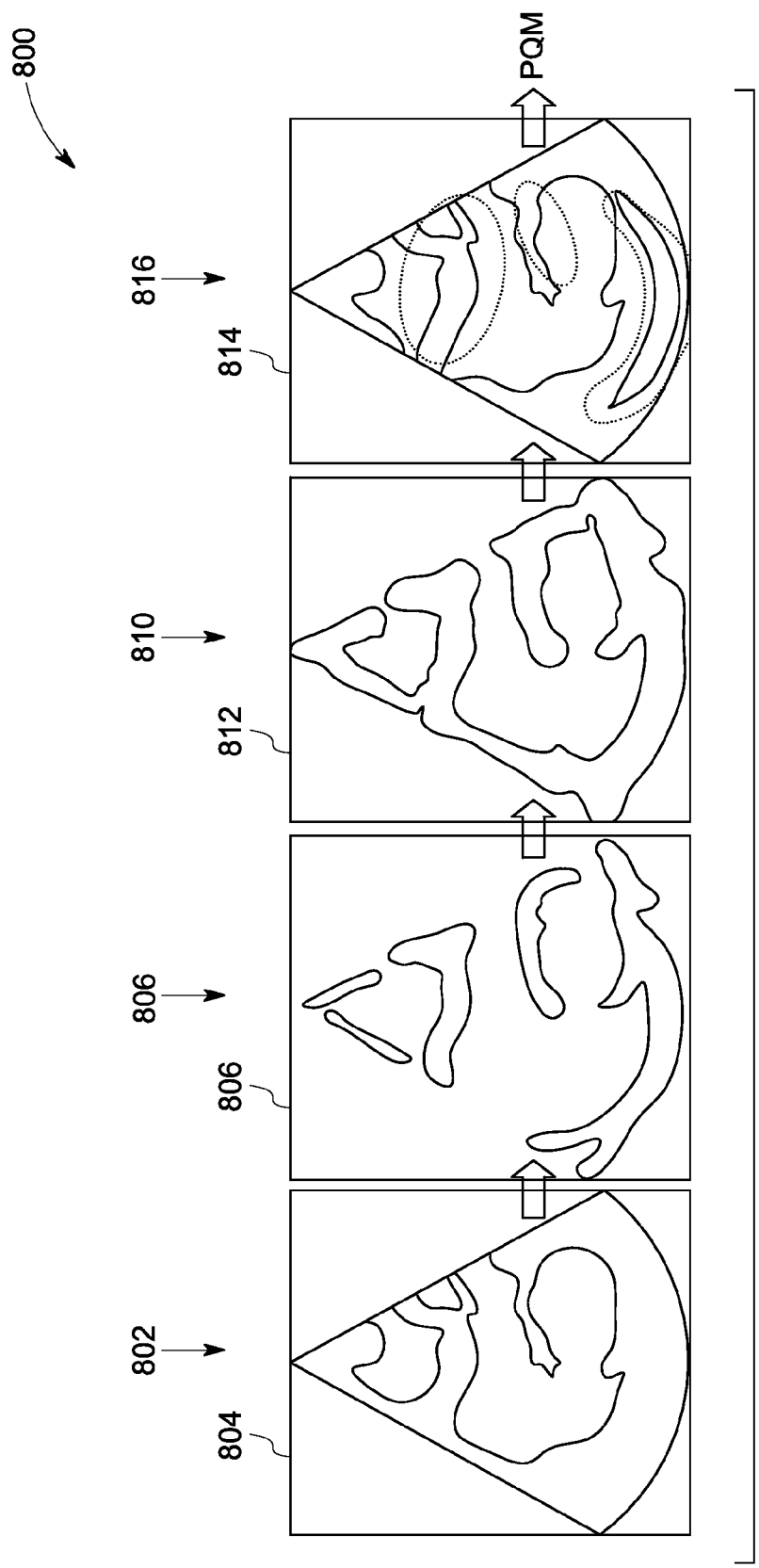
Figure 10:
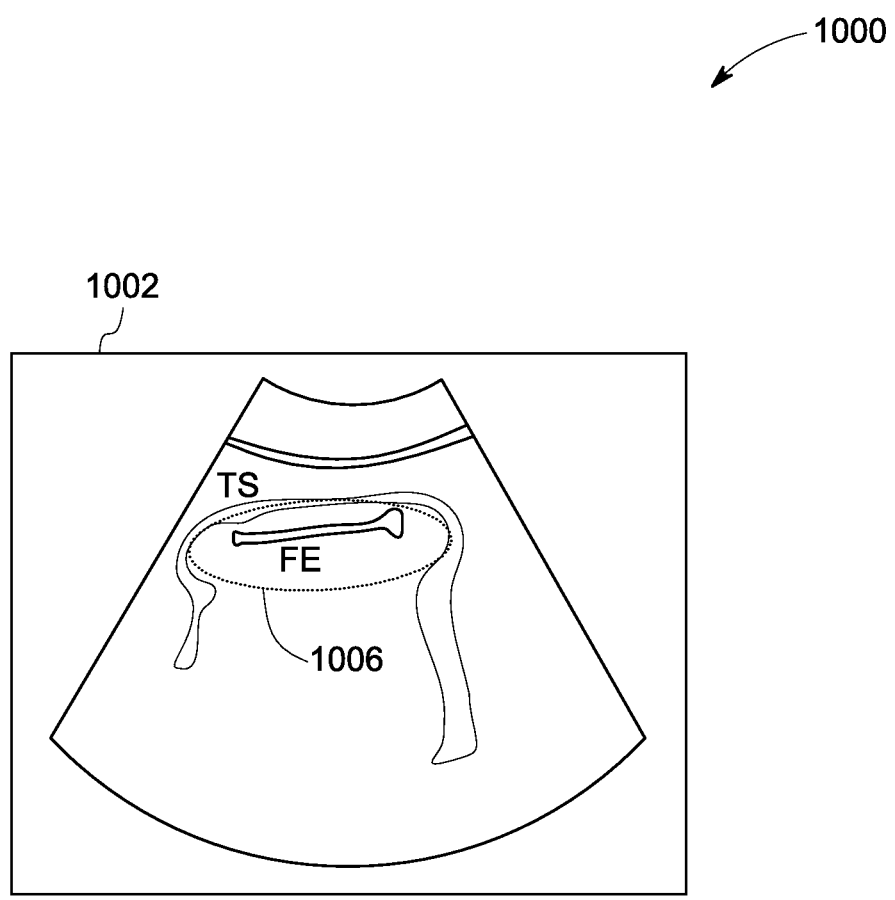
Figure 11:
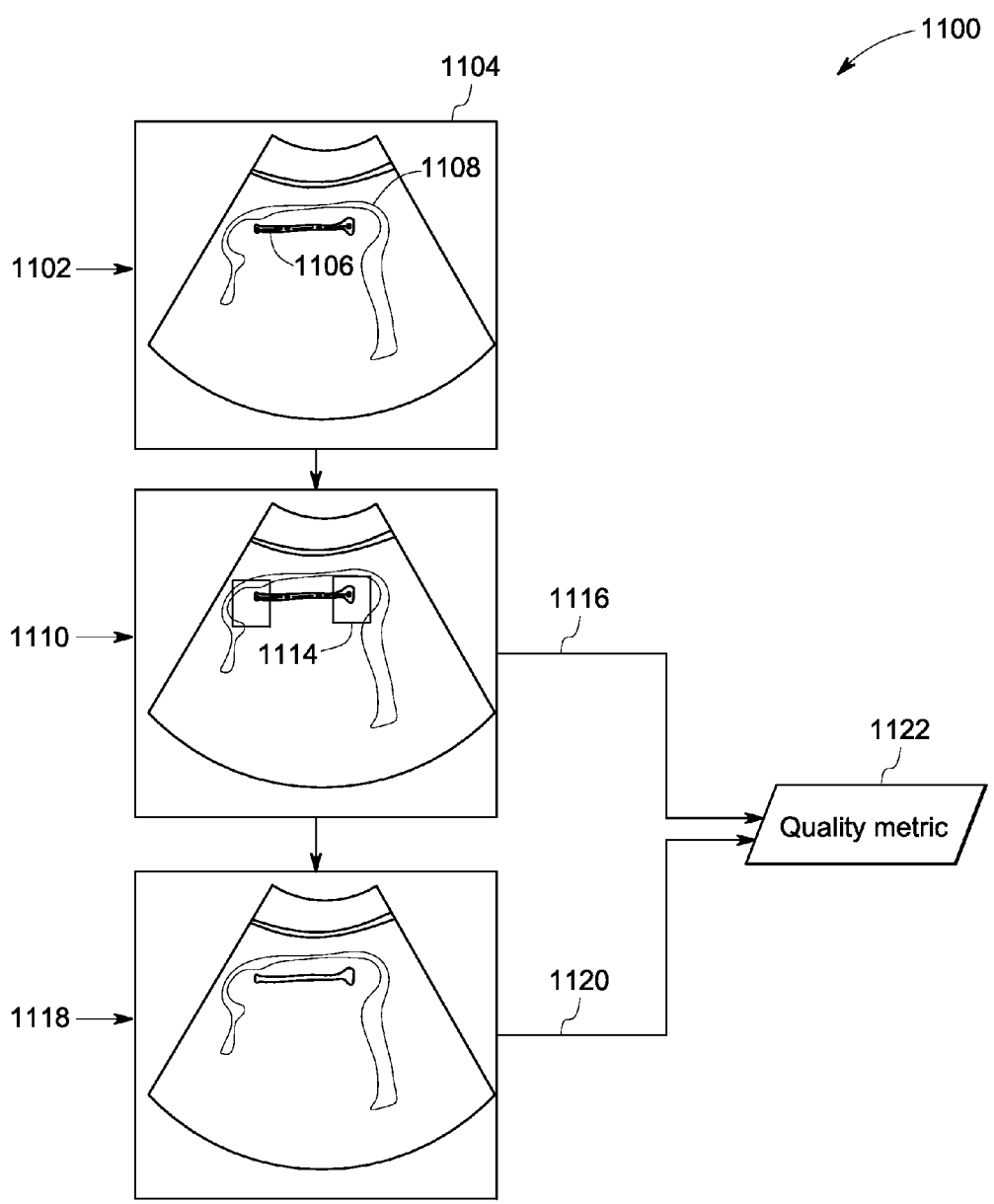
Figures 12A, 12B:
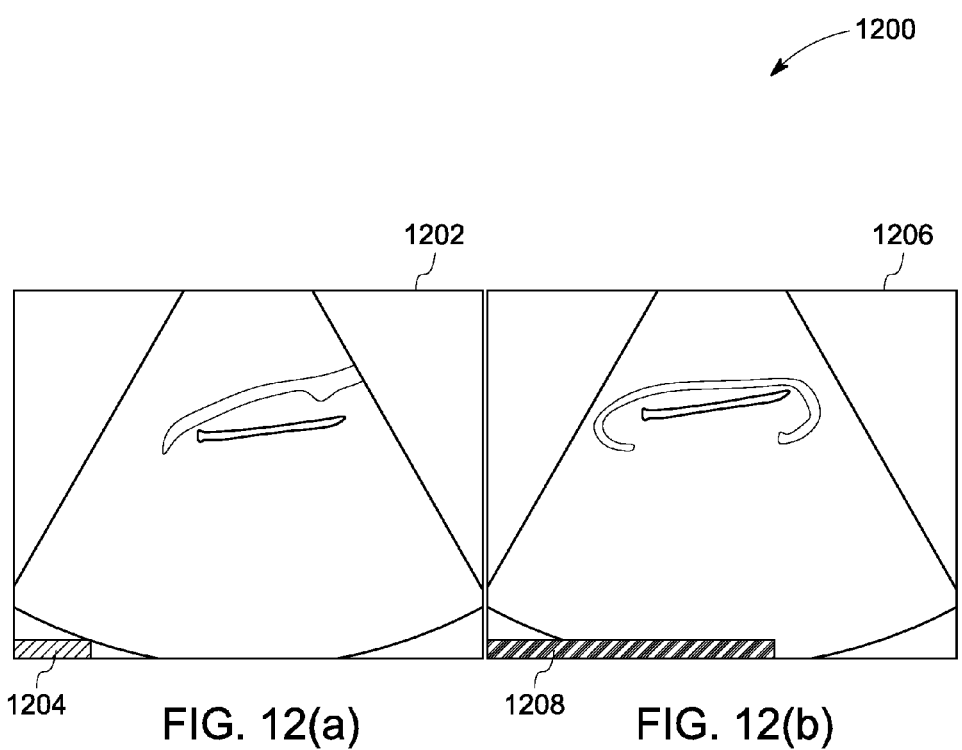
Figure 13:
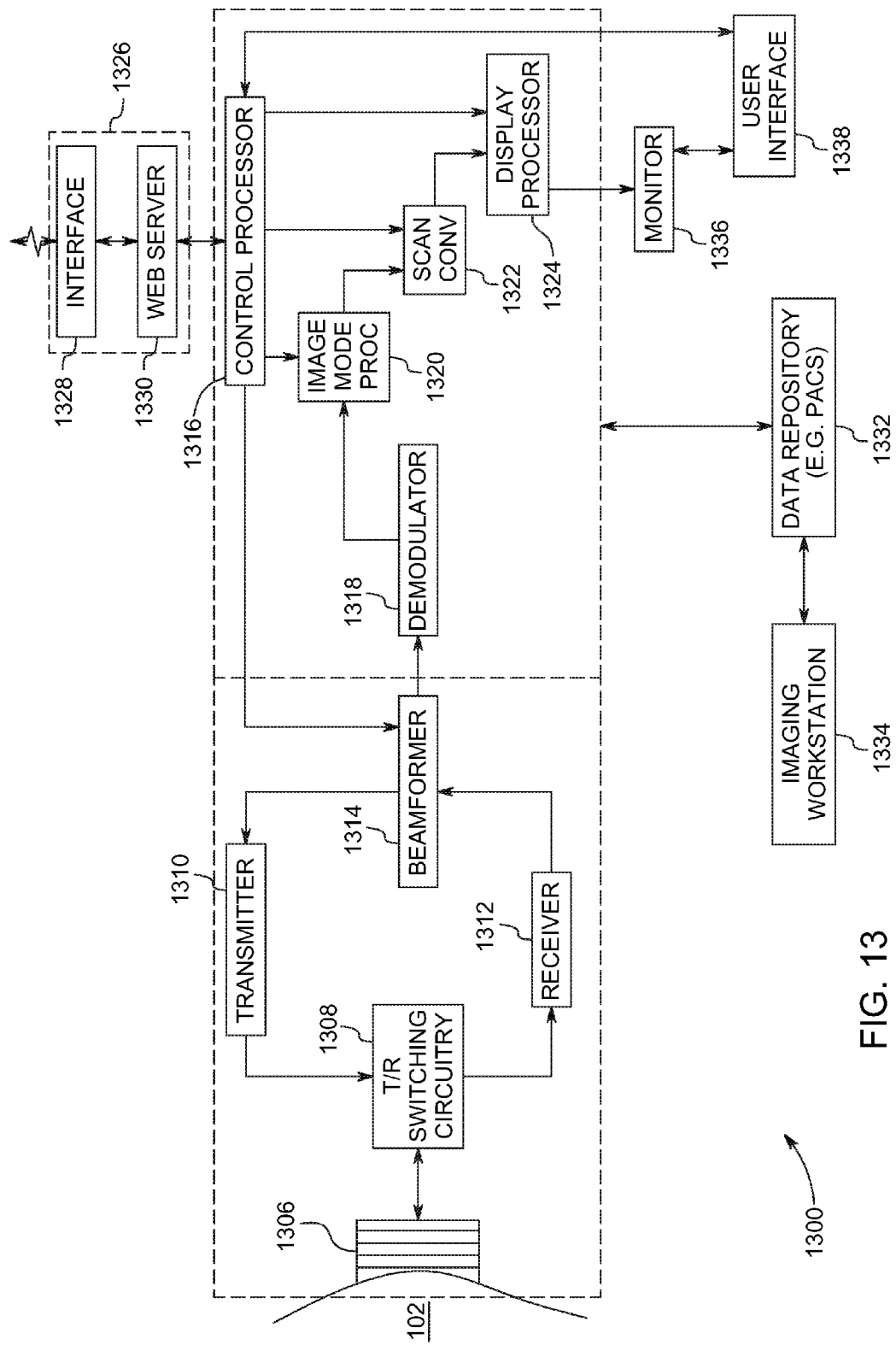

FIGS. 6(a) and 6(b) are diagrammatical illustrations of fetal head image frames along with a quality indicator, in accordance with aspects of the present technique;

FIG. 7 is a diagrammatical illustration of an image frame corresponding to a patient's heart in the parasternal long axis view;

FIG. 8 is a flow chart depicting an exemplary method for automated identification of an optimal image frame for ultrasound imaging of a heart, in accordance with aspects of the present technique;

FIGS. 9(a), 9(b) and 9(c) are diagrammatical illustrations of heart image frames along with a quality indicator, in accordance with aspects of the present technique;

FIG. 10 is a diagrammatical illustration of an image frame corresponding to a fetal femur;

FIG. 11 is a flow chart depicting an exemplary method for automated identification of an optimal image frame for ultrasound imaging of a fetal femur, in accordance with aspects of the present technique;

FIGS. 12(a) and 12(b) are diagrammatical illustrations of fetal femur image frames along with a quality indicator, in accordance with aspects of the present technique; and FIG. 13 is a diagrammatical illustration of an ultrasound imaging system for use in the system of FIG. 1.

DETAILED DESCRIPTION

As will be appreciated, during the process of ultrasound scanning, the clinician, such as a radiologist or a sonographer tries to capture a view of a certain anatomy, or a view which confirms or negates a particular condition. Once the radiologist is satisfied with the quality of the scan plane, the image is frozen to proceed to the measurement phase. To that end, acquisition of an "optimal" image frame or scan plane corresponding to an anatomical region of interest in correct scan planes is an important step towards accurate diagnosis. In accordance with exemplary aspects of the present technique, systems and methods configured to aid in enhancing ultrasound imaging workflow are presented. In particular, the methods and systems are configured to aid in the automated identification of an optimal image frame. Additionally, the system and methods are configured to generate an indicator for each image frame in real time, where the indicator is generally representative of a quality of the current image frame. Accordingly, the systems and methods described hereinafter are also configured to flag the most accurate scan plane frame and facilitate automated measurements using the optimal image frame. Moreover, once an image is frozen, the systems and methods are also configured to rate the scan plane quality before performing any measurement.

FIG. 1 is a block diagram of an exemplary system 100 for use in diagnostic imaging in accordance with aspects of the present technique. The system 100 is configured to aid a clinician such as a radiologist or an ultrasound technician in imaging an object of interest.

As will be appreciated, during a scanning procedure, the clinician, typically positions an ultrasound probe on or about a region of interest to be imaged. It may be noted that the object of interest may include a patient, a fetus, or a test object. During the scanning procedure, the clinician acquires a plurality of image frames corresponding to an anatomical region of interest in the object of interest. However, it is desirable to identify an optimal image frame that may be used to perform measurements. As used herein, the term optimal image frame is used to refer to a best possible image frame that has a desired image attribute in accordance with desired guidelines and hence may be used to perform any subsequent measurements. The desired guidelines may include clinical guidelines or industrial guidelines.

In particular, the system 100 is configured to determine a quality corresponding to each acquired image frame/plane. To that end, the system 100 is also configured to generate an indicator that is representative of the quality of each acquired image frame. Furthermore, as used herein, the term quality of the image frame is used to refer to a goodness of fit of a current image frame to a standard template for a specific view of an anatomical region of interest. Moreover, system 100 is also configured to communicate the indicator so generated to the clinician, thereby aiding the clinician in the imaging process. In particular, the indicator may be provided as feedback to the system 100 or the clinician. It may be noted that the indicator may be generated and provided to the clinician in real-time. Furthermore, it may be noted that in one example, the acquired image frame may include a two-dimensional (2D) image frame. Also, in certain embodiments, the image frames may include B-mode ultrasound images. Additionally, the 2D image frames may include static 2D image frames or cine loops that include a series of 2D image frames acquired over time. It may be noted that although the present technique is described in terms of 2D ultrasound images, use of the present technique with three-dimensional (3D) ultrasound images and four-dimensional (4D) ultrasound images is also envisaged.

In the present example, the object of interest may include a fetus in the patient 102. It may be noted that although the present technique is described with reference to a fetus as the object of interest, use of the present technique for imaging anatomical regions of interest in other objects of interest such as an adult patient is also envisaged. To that end, the system 100 may be configured to acquire image data representative of the fetus. In one embodiment, the system 100 may acquire image data from the fetus via an image acquisition device 104. Also, in one embodiment, the image acquisition device 104 may include a probe, where the probe may include an invasive probe, or a non-invasive or external probe, such as an external ultrasound probe, that is configured to aid in the acquisition of image data. Also, in certain other embodiments, image data may be acquired via one or more sensors (not shown) that may be disposed on the fetus. By way of example, the sensors may include physiological sensors (not shown) such as electrocardiogram (ECG) sensors and/or positional sensors such as electromagnetic field sensors or inertial sensors. These sensors may be operationally coupled to a data acquisition device, such as an imaging system, via leads (not shown), for example.

The system 100 may also include a medical imaging system 106 that is in operative association with the image acquisition device 104. It should be noted that although the exemplary embodiments illustrated hereinafter are described in the context of a medical imaging system, other imaging systems and applications such as industrial imaging systems and non-destructive evaluation and inspection systems, such as pipeline inspection systems, liquid reactor inspection systems, are also contemplated. Additionally, the exemplary embodiments illustrated and described hereinafter may find application in multi-modality imaging systems that employ ultrasound imaging in conjunction with other imaging modalities, position-tracking systems or other sensor systems. For example, the multi-modality imaging system may include a positron emission tomography (PET) imaging system-ultrasound imaging system. Furthermore, it should be noted that although the exemplary embodiments illustrated hereinafter are described in the context of a medical imaging system, such as an ultrasound imaging system, use of other imaging systems, such as, but not limited to, a computed tomography (CT) imaging system, a contrast enhanced ultrasound imaging system, an X-ray imaging system, an optical imaging system, a positron emission tomography (PET) imaging system, a magnetic resonance (MR) imaging system and other imaging systems is also contemplated in accordance with aspects of the present technique.

As noted hereinabove, in a presently contemplated configuration, the medical imaging system 106 may include an ultrasound imaging system. The medical imaging system 106 may include an acquisition subsystem 108 and a processing subsystem 110, in one embodiment. Further, the acquisition subsystem 108 of the medical imaging system 106 is configured to acquire image data representative of one or more anatomical regions of interest in the fetus via the image acquisition device 104, in one embodiment. For example, the acquired image data may include a plurality of 2D image frames or slices. Additionally, the image data acquired from the fetus may then be processed by the processing subsystem 110.

According to aspects of the present technique, the image data acquired and/or processed by the medical imaging system 106 may be employed to aid a clinician in identifying an optimal image frame for performing measurements. In one example, the system 100 may be configured to aid the clinician in the selection of the optimal image frame by providing an indicator that is representative of a quality of the current image frame. In certain embodiments, the processing subsystem 110 may be further coupled to a storage system, such as the data repository 114, where the data repository 114 is configured to store the acquired image data.

Furthermore, in accordance with exemplary aspects of the present technique, the processing subsystem 110 may include a rating platform 112 that is configured to aid in the automated identification of the optimal image frame corresponding to an anatomical region of interest. However, in certain embodiments, the rating platform 112 may also be configured to aid in the identification of the optimal image may entail manual intervention. More particularly, the rating platform 112 may be configured to generate a quality metric or score that is representative of the quality of the current image frame.

In accordance with exemplary aspects of the present technique, the rating platform 112 is configured to generate a quality metric corresponding to a 2D image frame that corresponds to an anatomical region of interest such that the quality metric conforms to clinical guidelines that are prescribed to observe the anatomical region of interest. For example, for imaging the heart, the clinical guidelines to acquire a good quality Parasternal Long Axis View (PLAX) may prescribe that features of interest such as the pericardium, the mitral valve and the septum be visible in the acquired image frame. Moreover, the quality metric may be generated such that the quality metric is representative of a functionally optimal image frame that allows a correct measurement and/or inference to be made. Furthermore, it is desirable that the indicator so generated and communicated to the clinician should be visually acceptable to the clinician. Additionally, rating platform 112 is further configured to communicate the generated quality metric to the clinician or the system 100, thereby aiding the clinician and/or the system 100 in selecting the optimal image frame for performing measurements. In one embodiment, the system 100 and more particularly, the rating platform 112 may be configured to provide feedback to the system 100 and/or the clinician in the form of an indicator. The indicator is generally indicative of the computed quality metric. Also, the terms quality metric and score may be used interchangeably.

As previously noted, the rating platform 112 may be configured to facilitate the identification of an optimal image corresponding to the anatomical region of interest employing the images acquired via the medical imaging system 106 and will be described in greater detail with reference to FIGS. 2-13. It may be noted that the anatomical region of interest may include any anatomy that can be imaged. For example, the anatomical region of interest may include the heart, and fetal features like the femur, the head, and the like. Also, the anatomical region of interest may include the heart in an adult patient, for example. Although the present technique is described in terms of identifying the optimal image frame corresponding to the anatomical region of interest in the fetus, it may be noted that use of the present technique for the determination of an optimal image frame corresponding to other anatomical regions of interest or other objects of interest is also envisaged.

Further, as illustrated in FIG. 1, the medical imaging system 106 may include a display 116 and a user interface 118. In certain embodiments, such as in a touch screen, the display 116 and the user interface 118 may overlap. Also, in some embodiments, the display 116 and the user interface 118 may include a common area. In accordance with aspects of the present technique, the display 116 of the medical imaging system 106 may be configured to display an image generated by the medical imaging system 106 based on the acquired image data. Additionally, in accordance with further aspects of the present technique, the optimal image frame identified by the rating platform 112 may be visualized on the display 116. Moreover, the quality metric generated by the rating platform 112 may also be visualized on the display 116. In one embodiment, the indicator that is representative of the quality metric may be overlaid on the corresponding image frame visualized on the display 116. For example, the generated indicator may be overlaid on or about the image visualized on the display 116.

In addition, the user interface 118 of the medical imaging system 106 may include a human interface device (not shown) configured to aid the clinician in manipulating image data displayed on the display 116. The human interface device may include a mouse-type device, a trackball, a joystick, a stylus, or a touch screen configured to facilitate the clinician to identify the one or more regions of interest requiring therapy. However, as will be appreciated, other human interface devices, such as, but not limited to, a touch screen, may also be employed. Furthermore, in accordance with aspects of the present technique, the user interface 118 may be configured to aid the clinician in navigating through the images acquired by the medical imaging system 106. Additionally, the user interface 118 may also be configured to aid in manipulating and/or organizing the displayed images and/or generated indicators displayed on the display 116.

Figure 2:
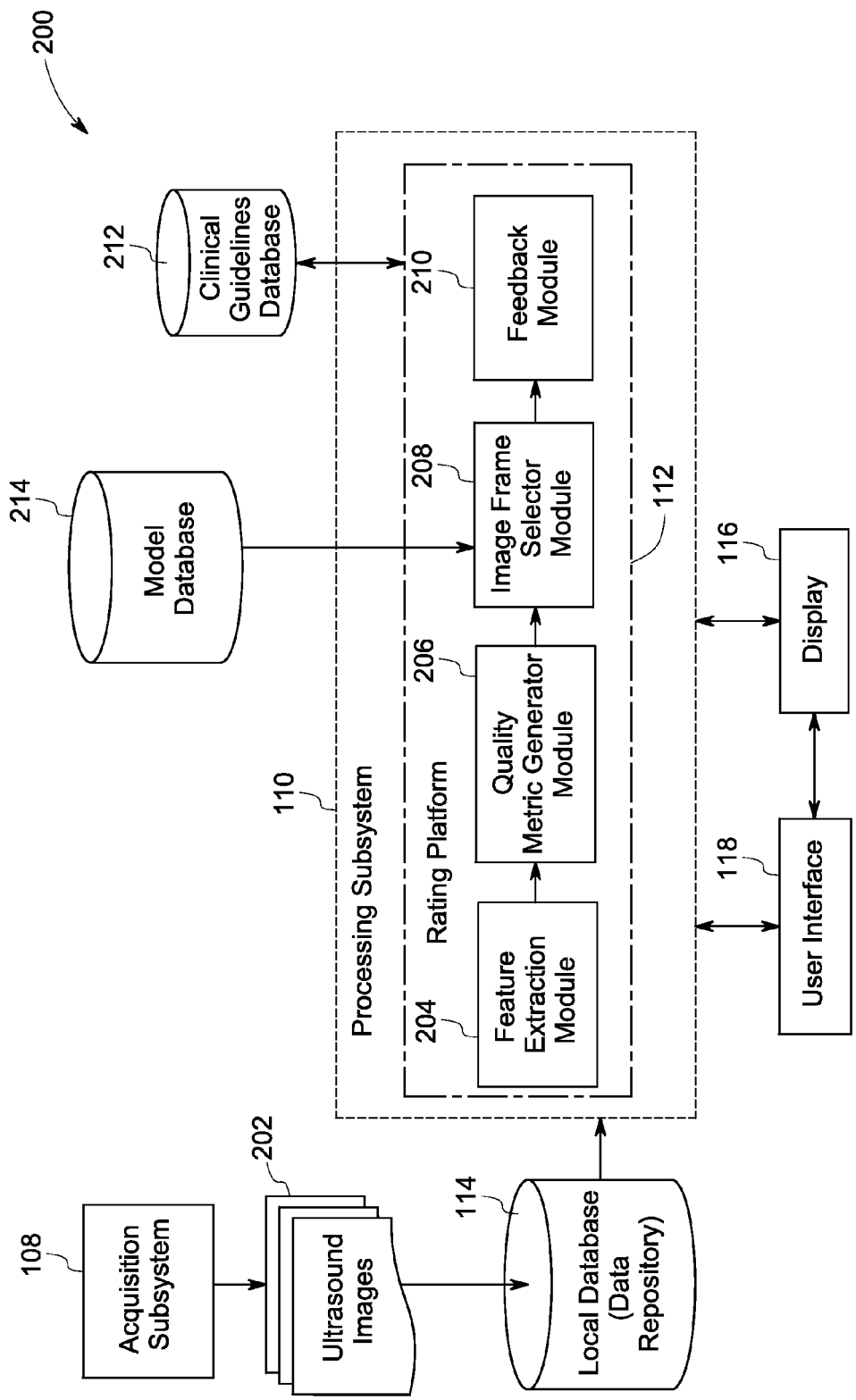
FIG. 2 is a diagrammatical illustration of one embodiment of the system of FIG. 1, in accordance with aspects of the present technique.

Turning now to FIG. 2, a block diagram 200 of one embodiment of the diagnostic system 100 of FIG. 1 is depicted. As previously noted with reference to FIG. 1, the acquisition subsystem 108 (see FIG. 1) is configured to aid in the acquisition of image data from the fetus in the patient 102 (see FIG. 1). Accordingly, one or more image data sets representative of the patient 102 may be acquired by the acquisition subsystem 108. In certain embodiments, the one or more image data sets may include ultrasound data 202. It may be noted that the ultrasound images 202 may be representative of an anatomical region in the fetus 102. For instance, in the example illustrated in FIG. 2, the ultrasound images 202 may include image data representative of the fetus or other patients. As previously noted, the ultrasound image data set 202 may include two-dimensional ultrasound image frames, in one example. Also, may include cine loops, where the cine loops include 2D image frames acquired over time t.

Furthermore, the image data acquired by the acquisition subsystem 108 may be stored in the data repository 114 (see FIG. 1). In certain embodiments, the data repository 114 may include a local database. The rating platform 112 (see FIG. 1) may then access these images, such as the ultrasound image data set 202, from the local database 114. Alternatively, the ultrasound image data set 202 may be obtained by the acquisition subsystem 108 from an archival site, a database, or an optical data storage article. For example, the acquisition subsystem 108 may be configured to acquire images stored in the optical data storage article. It may be noted that the optical data storage article may be an optical storage medium, such as a compact disc (CD), a digital versatile disc (DVD), multi-layer structures, such as DVD-5 or DVD-9, multi-sided structures, such as DVD-10 or DVD-18, a high definition digital versatile disc (HD-DVD), a Blu-ray disc, a near field optical storage disc, a holographic storage medium, or another like volumetric optical storage medium, such as, for example, two-photon or multi-photon absorption storage format. Further, the ultrasound image data set 202 so acquired by the acquisition subsystem 108 may be stored locally on the medical imaging system 106 (see FIG. 1). The ultrasound image data set 202 may be stored in the local database 114, for example.

Also, in the embodiments illustrated in FIGS. 1-2, the processing subsystem 110 is shown as including the rating platform 112, where the rating platform 112 is configured to aid in the identification of an optimal image frame employing the acquired ultrasound image data set 202, as previously described. However, in certain embodiments, the rating platform 112 may also be used as a standalone module that is physically separate from the processing subsystem 110 and the medical imaging system 106. By way of example, the rating platform 112 may be operationally coupled to the medical imaging system 106 and configured to aid in identification of the optimal image frame corresponding to the anatomical region in the fetus 102 using the acquired ultrasound images 202.

In one embodiment, the rating platform 112 may include a feature extraction module 204, a quality metric generator module 206, and an image frame selector module 208. It may be noted that although the configuration of FIG. 2 depicts the rating platform 112 as including the feature extraction module 204, the score generator module 206, the image frame selector module 208 and the feedback module 210, fewer or more number of such modules may be used.

The rating platform 112 may also include a feedback module 210, in certain embodiments. In accordance with aspects of the present technique, the feature extraction module 204 may be configured to process the acquired image frames 202 to extract one or more features of interest based upon the selected anatomical region of interest. For example, while imaging the fetal head, the feature extraction module 204 may be configured to extract an outline of the fetal head, if present, from the acquired image frames.

As will be appreciated, while scanning, it is desirable to aid the clinician in determining if a current 2D image frame is representative of an image frame is optimal to make a measurement. In accordance with aspects of the present technique, the rating platform 112 and in particular the quality metric generator module 206 is configured to generate a metric or score for the viability of the current image frame towards that end. Accordingly, the quality metric generator module 206 may be configured to compute a metric corresponding to the image frames based upon a quality of the image frames. As previously noted, the quality metric may be representative of a closeness of fit of the image frame to a predefined or determined model. To that end, the quality metric generator module 206 may be configured to retrieve a corresponding model from a model database 214 and compare the current image frame with the associated model to generate the quality metric. For example, if the anatomical region of interest includes the fetal head, the quality metric generator module 206 may be configured to retrieve a determined model of the fetal head from the model database 214 and compare a current image frame with the retrieved model to generate the quality metric.

With continuing reference to FIG. 2, the image frame selector module 208 may be configured to aid in selecting one or more image frames from the plurality of image frames 202. In one example, the image frame selector module 208 may configured to verify if a current image frame has an acceptable quality based on clinical guidelines and visual acceptability of the clinician and/or the system 100. It may be noted that the clinical guidelines may be obtained from the clinical guidelines database 212, in one example. If the current image frame does not meet the guidelines of acceptable view, then adjustments may be made to a position of a probe, such as the probe 104, to acquire other image frames.

As noted hereinabove, the quality metric generator module 206 is configured to generate a metric that is representative of the viability of the current image frame as the optimal image frame. Accordingly, it is desirable to provide a feedback to the clinician and/or the system 100 that is representative of the quality metric. The feedback module 210 is configured to provide a feedback that is symbolic of the quality metric to the clinician and/or the system 100. The symbolic feedback may include a display, in one embodiment. The display may be a color bar, a pie chart, a number, and the like that denote the quality of the image frame. Moreover, the feedback may be an audio feedback and/or an audio-visual feedback. In one example, the audio feedback may include one or more beeps or a voice in a language of choice. Additionally, feedback may be an 'auto-freeze' of the image frame. Furthermore, once the optimal frame is identified, an automated measurement may be triggered.

Figure 3:
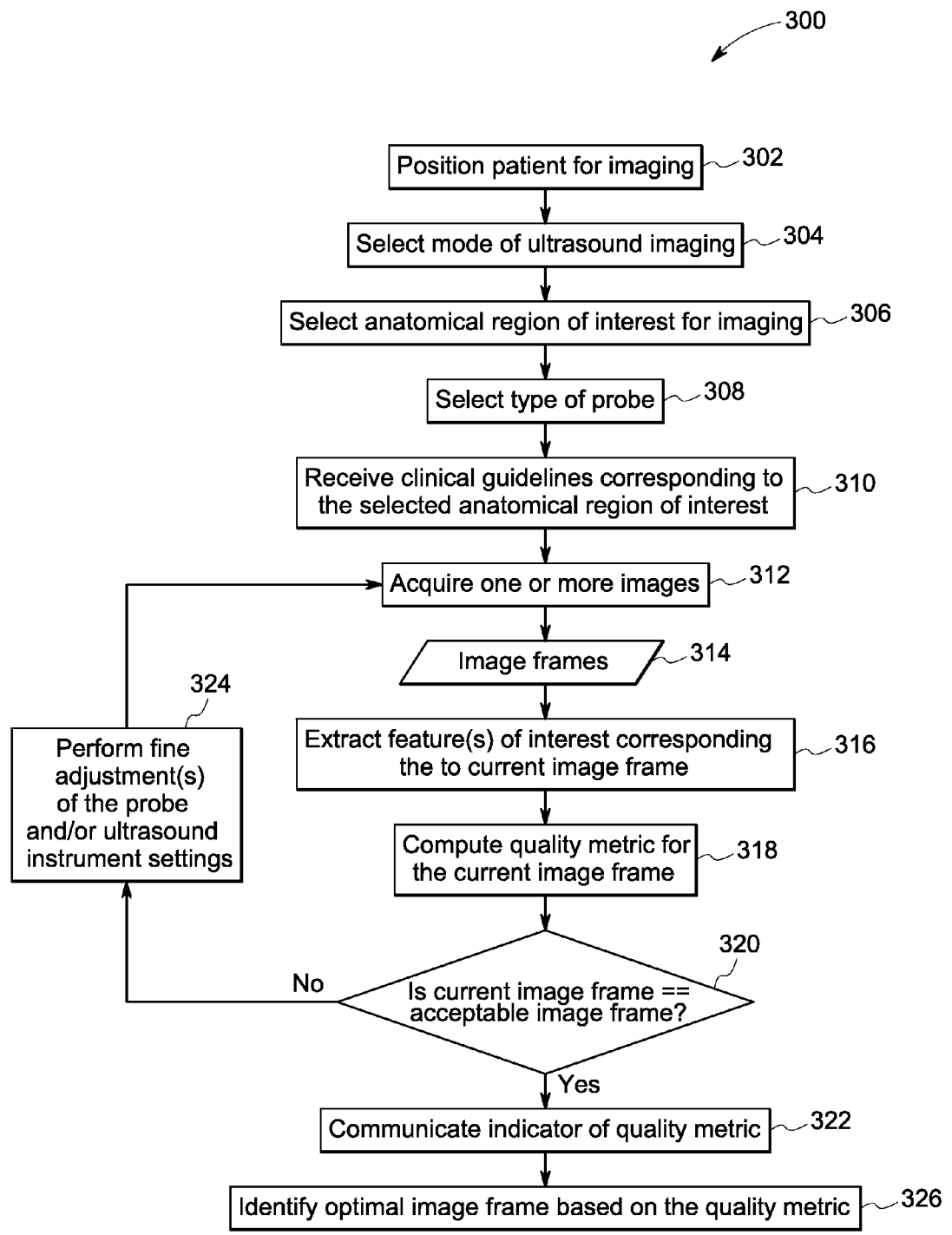
FIG. 3 is a flow chart depicting an exemplary method for automated identification of an optimal image frame for ultrasound imaging, in accordance with aspects of the present technique.

The working of the rating platform 112, and the working of the feature extraction module 204, the score generator module 206, the image frame selector module 208 and the feedback module 210, in particular, may be better understood with reference to the exemplary logic depicted in FIG. 3. Turning now to FIG. 3, a flow chart of exemplary logic 300 for a method for identifying an optimal image frame corresponding to an anatomical region of interest in the fetus is illustrated. It may be noted that the method of FIG. 3 is described in terms of the various components of FIGS. 1-2.

The method 300 may be described in a general context of computer executable instructions. Generally, computer executable instructions may include routines, programs, objects, components, data structures, procedures, modules, functions, and the like that perform particular functions or implement particular abstract data types. In certain embodiments, the computer executable instructions may be located in computer storage media, such as a memory, local to an imaging system 106 (see FIG. 1) and in operative association with a processing subsystem. In certain other embodiments, the computer executable instructions may be located in computer storage media, such as memory storage devices, that are removed from the imaging system. Moreover, the method for automated identification of an optimal image frame includes a sequence of operations that may be implemented in hardware, software, or combinations thereof.

As will be appreciated during a typical scan session, an object of interest such as a patient is positioned for imaging and the clinician attempts to image a desired anatomical region of interest in the patient. Accordingly, the method starts at step 302 where a patient is positioned for imaging. Subsequently, at step 304, a mode of ultrasound imaging may be selected. For example, "obstetric ultrasound" may be selected as the mode of ultrasound imaging if it is desirable to image a fetus. Alternatively, "cardiac ultrasound" may be designated as the mode of ultrasound imaging if it is desirable to image the cardiac region of the patient. It may be noted that in one embodiment, the clinician may select the mode of imaging, while in certain other embodiments, the system 100 may be configured to select the mode of imaging.

Following the selection of the mode of ultrasound imaging, an anatomical region of interest for imaging may be selected, as depicted by step 306. In one example, the clinician may identify the anatomical region of interest in the fetus to be imaged, where the anatomical region of interest may include the heart, the head and/or the femur in the fetus. Subsequent to the selection of the anatomical region of interest, a probe that is appropriate for imaging the selected anatomical region of interest may be selected, as generally indicated by step 308.

In accordance with aspects of the present technique, the identification of the optimal image frame may be performed in alignment with determined clinical guidelines for imaging the selected anatomical region of interest. Accordingly, at step 310, the determined clinical guidelines corresponding to the selected anatomical region of interest may be received. As previously noted, the clinical guidelines corresponding to the anatomical region of interest may be received from the clinical guidelines database 212 (see FIG. 2). By way of example, the clinical guidelines associated with imaging the head in the fetus may entail verification of presence of the head, the midline falx, the thalami and the cavum septum pellucidum (CSP).

Furthermore, as indicated by step 312, one or more images 314 corresponding to the anatomical region of interest in the fetus may be acquired. As previously noted, the one or more images 314 may include 2D image frames. Also, in certain embodiments, the 2D image frames may include B-mode image frames. Moreover, the 2D image frames 314 may be acquired via use of the probe selected at step 308 positioned on or about the anatomical region of interest in the fetus. It may be noted although at this junction in the workflow, the clinician is aware of a current location of the probe or the anatomical region of interest, however, an image frame for performing measurements may not be frozen. By way of example, for imaging a fetal head, a plurality of image frames corresponding to the head region in the fetus may be acquired in conformance with the clinical guidelines at step 310. However, it is desirable to select and/or freeze an optimal image frame in accordance with the received clinical guidelines to make any subsequent measurements for diagnosis.

In accordance with exemplary aspects of the present technique, the optimal image frame may be identified from the acquired plurality of image frames 314. As previously noted, the optimal image frame is representative of an image frame that may be used to perform measurements. To that end, at step 316, one or more features of interest may be extracted from each acquired image frame 314. Accordingly, the one or more features of interest may be extracted from a current image frame. It may be noted that the features of interest correspond to the selected anatomical region of interest. By way of example, if the anatomical region of interest includes the head of the fetus, then the features of interest may include the midline falx, the paired thalami, and/or the cavum septum pellucidum (CSP). In a similar fashion, if the anatomical region of interest includes the fetal femur, then the features of interest may include the femur shaft and the thigh skin. The feature extraction module 204 of FIG. 2 may be employed to extract the one or more features of interest. Step 316 will be described in greater detail with reference to FIGS. 4-12.

Furthermore, at step 318, a score or quality metric representative of a quality of the current image frame may be generated. In accordance with aspects of the present technique, the quality metric may be generated based on the anatomical region of interest. In one embodiment, the quality metric generator module 206 of FIG. 2 may be employed to generate the quality metric for the current image frame. The generation of the score corresponding to the current image frame will be described in greater detail with reference to FIGS. 4-12.

Additionally, at step 320, a check may be carried out to verify if the current image frame is representative of an acceptable image frame. As used herein, the term acceptable image frame may be representative of an image frame that is visually acceptable to the clinician and/or the system 100. It may be noted that in certain embodiments, the image frame selector module 208 may be configured to verify if the current image frame is an acceptable image frame may be based on the score generated at step 318. It may be noted that the image selector module 212 may be used to identify the optimal image frame. The selection of the optimal image frame will be described in greater detail with reference to FIGS. 4-12.

At step 320, if it is determined that the current image frame is representative of an acceptable image frame, an indicator that is symbolic of the metric or score may be generated and communicated to the clinician, as indicated by step 322. In one embodiment, the indicator may be a visual indicator, an audio indicator or both a visual indicator and an audio indicator that denotes the quality of the current image frame. The visual indicator may include a color bar, a pie chart, a number, and the like. Also, the audio indicator may include one or more beeps, a voice in a language of choice, and so on. However, a combination of an audio indicator and a visual indicator may be employed. In accordance with further aspects of the present technique, the indicator may entail an 'auto-freeze' of the current image frame. Furthermore, the indicator may also facilitate an automated measurement utilizing the optimal image frame. The indicator may be generated and communicated to the clinician by the feedback module 210 (see FIG. 2), in one example. Subsequently, an optimal image frame corresponding to the anatomical region of interest may be identified based on the quality metric and/or the indicator, as depicted by step 326.

With continuing reference to step 320, if it is determined that the current image frame is not indicative of an acceptable image frame, then fine adjustments may be made to a position of the probe, as depicted by step 324. By way of example, fine adjustments may be made to the probe axis with respect to the fetus. In addition, at step 324, adjustments to the ultrasound instrument settings may also be made. Control may then be passed to step 312 and steps 312-324 may be repeated until an image frame of optimum quality is obtained.

The method of FIG. 3 may be better understood with reference to FIGS. 4-12. In particular, the process of identification of the optimal image frame is described with reference to the selection of the optimal image frame for imaging the heart, the head in the fetus, and the femur in the fetus.

Figure 4:
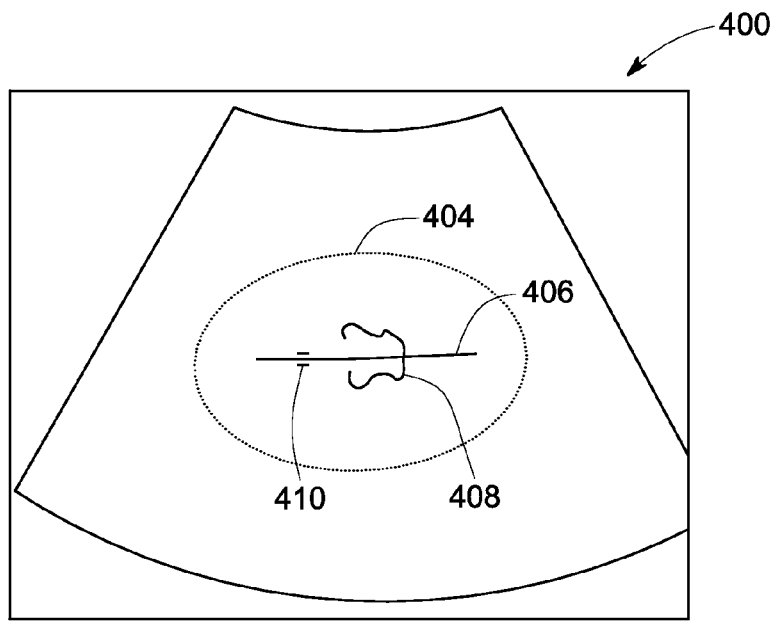
FIG. 4 is a diagrammatical illustration of an image frame corresponding to a fetal head.

Referring now to FIG. 4, a diagrammatical representation 400 of an optimal ultrasound image 402 for imaging the fetal head in accordance with the clinical guidelines corresponding to imaging the fetal head. For identifying the optimal image frame corresponding to the fetal head, in accordance with the clinical guidelines it may be desirable to verify the presence of one or more landmarks in the image frame 402. By way of example, the landmarks for imaging the fetal head may include an outline of the fetal head 404, a midline falx 406, paired thalami 408, and a cavum septum pellucidum (CSP).

Figure 5:
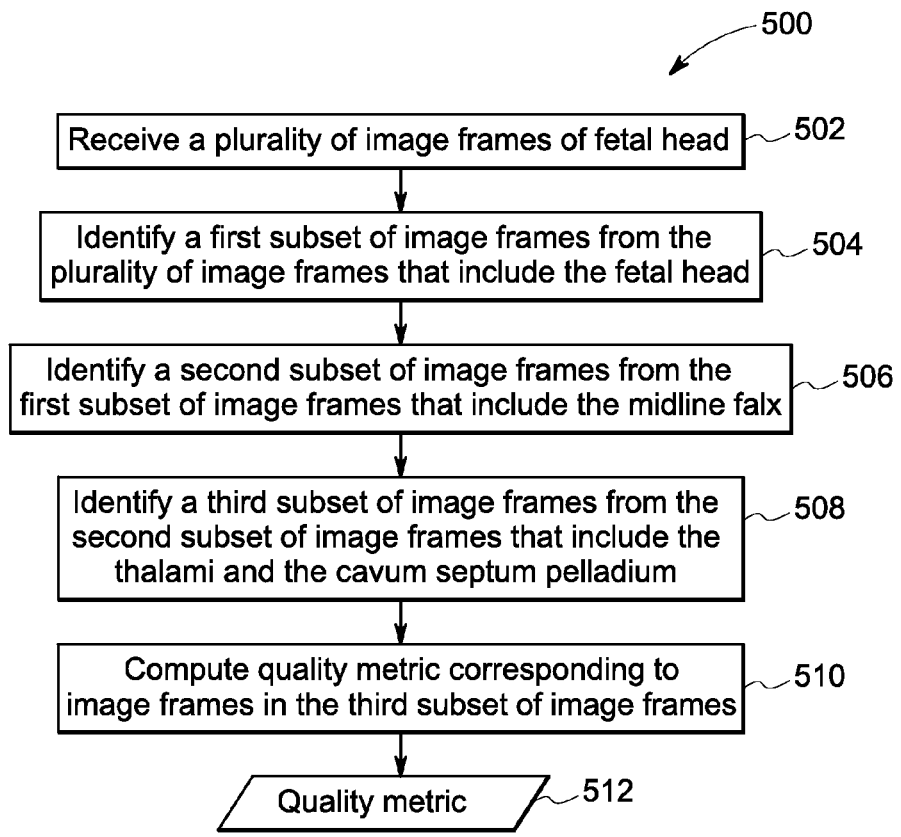
FIG. 5 is a flow chart depicting an exemplary method for automated identification of an optimal image frame for ultrasound imaging of a fetal head, in accordance with aspects of the present technique.

In accordance with aspects of the present technique, a method for identifying an optimal image frame while imaging a fetal head is presented in FIG. 5. FIG. 5 is a diagrammatical representation 500 of a method for identifying an optimal image frame while imaging a fetal head. The method starts at step 502 where the plurality of image frames 314 (see FIG. 3) may be received. Subsequently, at step 504, the plurality of image frames may be processed to verify for presence of a fetal head. Particularly, a first subset of image frames that includes the fetal head may be identified and selected. Also, image frames that do not include the fetal head may be rejected. In one embodiment, each image frame in the plurality of image frames 314 may be processed to identify and segment an elliptical object that may be representative of the fetal head. Consequent to this processing, the fetal head may be segmented, thereby localizing the fetal head. Furthermore, the first subset of image frames that includes the fetal head may be identified.

Once the first subset of image frames that includes the fetal head is identified, each of the image frames in the first subset may be further processed to generate a corresponding quality metric. To that end, in accordance with aspects of the present technique, each of the image frames in the first subset may be processed to verify presence of a midline falx, as depicted by step 506. Accordingly, image frames that include the midline falx may be identified and selected, while the image frames devoid of the midline falx may be rejected. In one embodiment, the presence of the midline falx in each image frame may be verified by extracting an interior region of fetal head. Subsequently, an edge detection filter may be applied. In one example, the edge detection filter may include phase congruency applied on a normalized image. Moreover, the midline falx may be extracted based on a cost function that measures the symmetry of the midline falx with respect to the cranium and an orientation of the midline falx. More particularly, a second subset of image frames that includes the midline falx may be selected from the first subset of image frames. This process aids in localizing the image frames, thereby reducing the scan time.

Following the verification of the presence of the midline falx, the second subset of image frames may be identified. Subsequently, at step 508, the second subset of image frames may be further processed to verify the presence of other landmarks. These other landmarks may include the paired thalami and the CSP. In one example, the presence of other landmarks such as the paired thalami and the CSP may be verified by comparing the image frames in the second subset of image frames with a corresponding model. Moreover, in one example, the model may be generated as an average of shapes and/or appearances of the anatomical region of interest. To that end, the model may be retrieved from the model database 214 of FIG. 2. In one example, the model corresponding to the thalami and the CSP may be retrieved. Subsequently, the current image frame from the second subset of image frames may be compared with the corresponding model. If the current image frame substantially matches the corresponding model, then that current image frame may be identified as including the desired features and may be assigned a relatively high score. Alternatively, if the current image frame does not substantially match the corresponding model, then that current image frame may be assigned a relatively lower score. It may be noted that this process may also be employed to process a cine loop of image frames.

Consequent to the processing of step 508, a third subset of image frames may be identified from the second subset. Once the third subset of image frames is selected based on the presence of the desired landmarks, a quality metric or score corresponding to each image frame in the third subset may be computed, as indicated by step 510. As previously noted, the quality metric is representative of a quality of the image frame. In the present example, the quality metric is representative of the presence of the landmarks in the image frame of interest. In accordance with aspects of the present technique, each image frame may be compared with a determined model and the quality metric may be generated based on this comparison. As previously noted, the quality metric may be representative of a closeness of fit of the image frame to the determined model. Subsequently, an image frame having a highest quality metric may be identified as the optimal image frame. In one embodiment, the image selector module 208 may be used.

Ensuing the generation of the quality metric, an indicator that is representative of the quality metric may be communicated to the system 100 or the clinician to aid in the selection of the optimal image frame. By way of example, the quality metric may be visually displayed/overlaid on the current image frame in the form of a quality indicator bar. The value of the quality metric may be manifested in the form of a color of the quality bar. This process may be repeated for each image frame in the third subset of image frames. Reference numeral 512 is generally representative of a quality metric generated consequent to the processing of steps 502-510. In accordance with aspects of the present technique, the quality bar may be configured to be responsive to the image change based on probe movement. It may be noted that since only a relatively small subset (third subset) of image frames are processed to generate the quality metric, the scan time may be minimized, thereby enhancing the clinical workflow.

As noted hereinabove, in the example where the acquired images include a plurality of single image frames, a quality metric corresponding to each image frame is generated. However, in certain embodiments, the acquired images may include a sequence of image frames or a cine loop of image frames. In this situation, a quality metric corresponding to each image frame in the cine loop may be generated. In accordance with aspects of the present technique, frame clustering may be employed to aid in identifying the optimal image frame. By way of example, in the case of cine loops, the quality metric may incorporate temporal information. To that end, a cluster of neighboring image frames of the current image frame may be identified. Subsequently, a cluster score corresponding to each image frame may be generated. In one example, the cluster score associated with each image frame may be dependent on the quality metrics corresponding to the neighboring image frames. Consequently, the quality metric associated with each image frame is weighted by the quality of the neighboring frames. It may be noted that if the quality metric corresponding to the neighboring image frames of the current image frame is high, higher is the probability for the current image frame to be representative of the optimal image frame.

An indicator representative of the quality metric may be generated and communicated by the system 100, thereby aiding in the selection of the optimal image frame during an imaging session. In accordance with aspects of the present technique, the indicator may include a visual indicator such as, but not limited to, quality bar, a pie chart, a numeric value and the like an/or an audio indicator in the form of a voice, a sound and the like. In one example, the indicator may be overlaid on the current image frame.

FIG. 6 is a diagrammatical representation 600 of an output of the method for identifying an optimal image frame corresponding to the fetal head. FIG. 6(a) is representative of a first image frame 602 of the fetal head. Also, in this example, a quality metric representative of a quality of the first image frame is represented in the form of a quality bar 604 that is superimposed on the first image frame 602. This quality bar 604 is indicative of the fact that the first image frame 602 may not be representative of an optimal image frame and it may be desirable to acquire other image frames.

In FIG. 6(b), a second image frame 606 of the fetal head is represented. Here again, an indicator of the quality metric corresponding to the second image frame 606 is represented in the form of a quality bar 608 that is superimposed on the second image frame 606. In the example of FIG. 6(b), the quality bar 608 indicates that this image frame 606 may be representative of an optimal image frame. In the example of FIG. 6, the quality indicators 604, 608 have a horizontal orientation and are superimposed along a lower border of the image frames 602, 606. However, the quality bars 604, 608 may be superimposed at other convenient locations. Accordingly, based on the feedback provided by the indicators 604, 608, the clinician or the system 100 may decide if it is desirable to acquire more image frames of the fetal head, thereby reducing scan time and enhancing the imaging workflow.

In the examples of FIGS. 6(a) and 6(b), the quality bars 604, 608 may be color quality bars. One or more colors may be used in the quality bar to represent the quality of the image frame. By way of example, the quality bar 604 of FIG. 6(a) may be a smaller red bar, while the quality bar 608 of FIG. 6(b) may be a longer bar with a green color. Accordingly, it may be desirable to select the image frame 606 that corresponds to the longer color quality bar with green color 608 as the optimal image frame. It may be noted that the workflow to provide the feedback described with reference to FIGS. 5-6 entails use of the steps 504, 506, 508 working in a serial fashion to down select the number of image frames, thereby enhancing the ease of identifying the optimal image frame.

In accordance with further aspects of the present technique, while imaging the heart, an optimal image frame may be identified. FIG. 7 is a diagrammatical representation 700 of an image frame of the heart. In particular, the image frame of FIG. 7 is representative of a Parasternal Long Axis (PLAX) view of the heart. It may be noted that the in accordance with aspects of the present technique, the method for identifying an optimal image frame corresponding to the heart may also find application in the imaging of a fetal heart or the heart of a child.

Reference numeral 702 is generally representative of a PLAX view corresponding to the heart. It may be noted that at the right scan plane and with optimal ultrasound instrument settings, it is desirable to identify/verify the presence of one or more anatomical landmarks. These anatomical landmarks may include the pericardium 704, the posterior wall 706, the right ventricular outflow tract 708, the septum 710, the aortic valve 712, the left ventricle 714, the mitral valve 716, the left atrium 718, the descending aorta 720, and the like.

Turning now to FIG. 8, a diagrammatical representation 800 of a method for identifying an optimal image frame corresponding to the heart is presented. It may be noted, the method is configured to automatically determine a quality of a plurality of image frames corresponding to the heart. In one example, the plurality of image frames may include Parasternal Long Axis (PLAX) B-mode echocardiograms.

It may be noted, that with optimal instrument settings, it may be desirable to verify that the long axis of the left ventricle 714 is oriented horizontally in a standard PLAX view (see FIG. 7). Additionally, it is also desirable that the posterior wall 706, the pericardium 704 and the septum 710 are substantially parallel to each other. Any deviation from this may be attributed to an incorrect scan plane or sub-optimal instrument settings. For example, a poor quality image may be due to sub-optimal instrument settings such as gain. Also, non-parallel septum 710 and pericardium 704 may be indicative of the fact that the scan plane failed to pass through the center of left ventricle 714. Also, in another example, a missing pericardium may complicate the measurement of the thickness of posterior wall 704 and diagnosis of pericardial effusion.

The method starts at step 802, where an image frame 804 representative of the heart is received. As noted hereinabove, in one example, the received image frame 802 may be representative of a PLAX view. According to aspects of the present technique, the method for identifying the optimal image frame entails verifying, in real-time, the presence of one or more features of interest. In one example, the features of interest may include tube-like structures corresponding to the septum 710, the mitral valve 716 and the pericardium 704. It may be noted that if the three features of interest such as the septum 710, the mitral valve 716, and the pericardium 704 are visible in an image frame, that image frame may be assumed to have a desired quality. Accordingly, the image frame 804 may be processed to enhance the contrast of the features of interest, as depicted by step 806. In one embodiment, the image frame 804 may be processed via a Frangi vesselness filter to enhance the contrast of the features of interest. Particularly, the image frame 804 may be filtered using the Frangi vesselness filter to mitigate any intensity inhomogeneity to generate an intermediate image such as a vesselness image frame 808. As will be appreciated, the Frangi vesselness filter is a vessel enhancement filter that is used to enhance the contrast of tubular structures with respect to the background. The intensity inhomogeneity is substantially reduced in the vesselness image frame 808.

Subsequently, at step 810, the vesselness image frame 808 may be processed to generate a binary image 812. It may be noted that in the vesselness image frame 808, in addition to the tubular structures of interest, there may exist regions of near-field haze and boundary artifacts. Therefore, it is desirable delete any undesirable regions from the vesselness image frame 808. To that end, the vesselness image frame 808 may be thresholded to generate the binary image 812. This binary image 812 may include the three features of interest, such as the septum 710, the mitral valve 714 and the pericardium 704 in addition to the other regions of the heart and imaging artifacts.

Once the segmented binary image 812 is generated, the binary image may be compared with a determined or predefined model to generate a quality metric that is indicative of a quality of the binary image 812 corresponding to the current image frame 804, as depicted by step 814. In one example, the determined or predefined model may include an atlas that defines the desired areas or features of interest. The atlas may be generated by manually segmenting the features of interest in PLAX images, in one embodiment. Alternatively, in certain other embodiments, the atlas may be generated by obtaining an average representation of the features of interest in PLAX images. In one example, a shape-based averaging algorithm such as the Rohlfing and Maurer's Shape based averaging technique may be used to generate the atlas.

Moreover, in one example, the comparison of the binary image 812 with the atlas or determined model may be performed based on the Generalized Hough Transform (GHT). It may be noted that the GHT may be used to detect the presence of objects of interest in the binary image 812. In the present example, the objects of interest may include the tube-like structures corresponding to the septum 710, the mitral valve 716 and the pericardium 704. Furthermore, during a matching phase, in accordance with aspects of the present technique, it may be desirable to find the most probable location of the atlas on the binary image 812. For example, a pixel with the maximum intensity in an accumulator A may be representative of the most probable location of a reference point. Furthermore, the maximum value of the accumulator A may be output as the PLAX quality metric (PQM) 818. The quality metric 818 may be representative of a closeness of fit of the binary image 812 to the atlas or determined model.

Additionally, it may be noted that the number of pixels corresponding to the septum, the mitral valve, and the pericardium in the PLAX atlas is different. Consequently, the number of votes received from each of these features of interest is different. In accordance with aspects of the present technique, it is desirable to appropriately weight the votes received from the septum, the mitral valve and the pericardium to ensure that the contributions from the features of interest are comparable. To that end, scalar weights $w_1$, $w_2$ and $w_3$ may be assigned such that the maximum contribution of the votes from any of the features of interest does not exceed a value of 1. Accordingly, the PQM metric 818 can vary between a value of 0 and 3. Moreover, in one example, the scalar weights $w_1$, $w_2$ and $w_3$ may be set to an inverse of the number of pixels corresponding to the septum, the mitral valve and the pericardium in the PLAX atlas, respectively.

Figure 9:
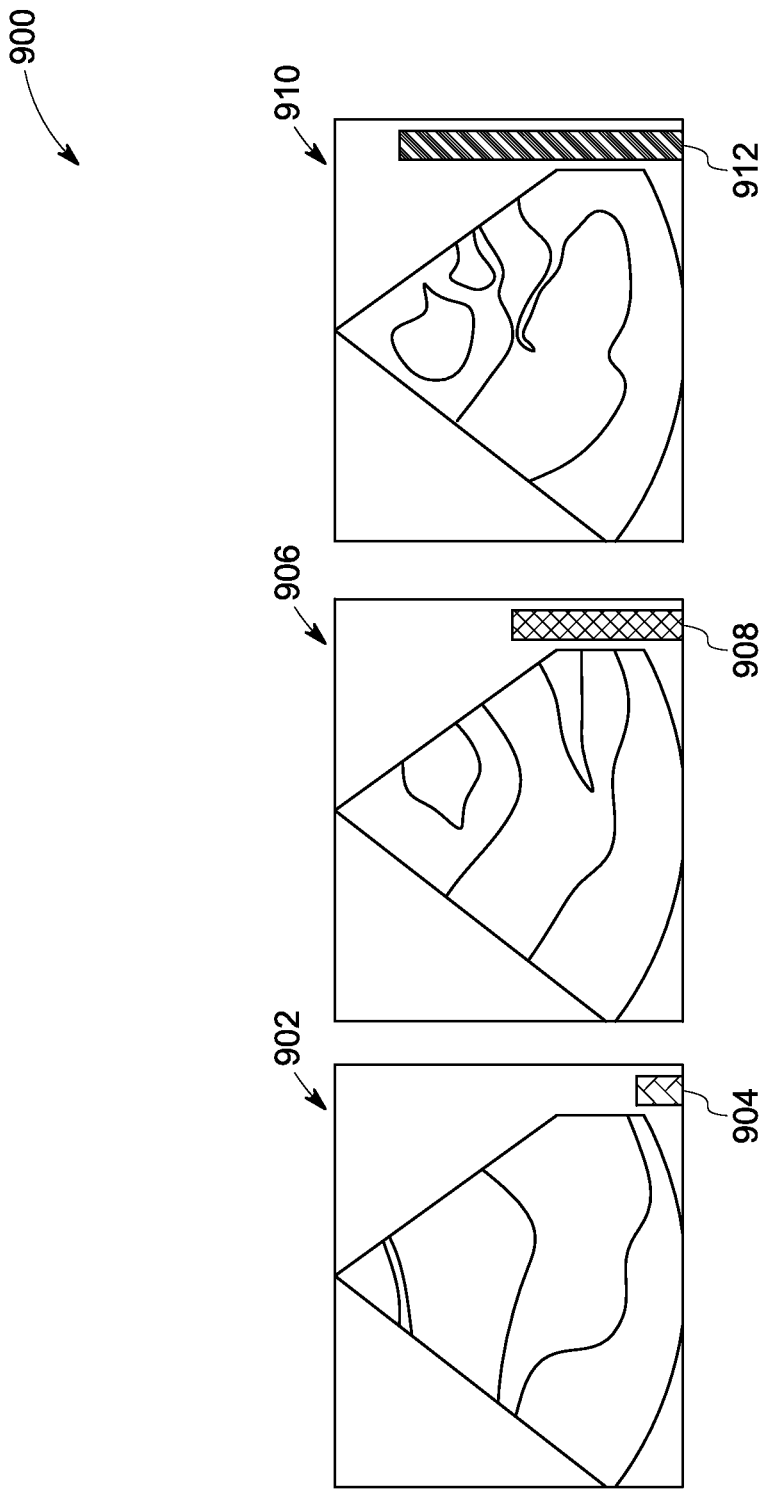

Once the quality metric 818 is generated, an indicator of the quality metric 818 may be generated and communicated to the clinician or the system. As previously noted, the indicator may be in the form of a quality bar that is superimposed on the current image frame on the display of the imaging system. FIG. 9 is generally representative of a display 900 of the indicator in the form of a quality bar that is superimposed on the image frames representative of the heart. In this example, the quality indicator has a vertical orientation and is superimposed along a right border of the image frames. However, the quality bar may be superimposed at other convenient locations. It may be noted that the height of the quality bar may be proportional to the PQM 818 computed for an image frame.

In the examples of FIGS. 9(a), 9(b) and 9(c), reference numerals 902, 906 and 910 are representative of a first image frame, a second image frame and a third image frame. The corresponding quality bars may be represented by reference numerals 904, 908 and 912 respectively. In this example, the quality bar may be a color quality bar. As is evident from the three image frames 902, 906, 910, a quality of the image frames improves from image frame to image frame as indicated by the quality bars 904, 908, 912. For example, the quality bar 912 of FIG. 9(c) may be a longer bar with green color and hence may be representative of the optimal image frame as opposed to the image frames of FIGS. 9(a) and 9(b) based on the corresponding quality bars. Accordingly, it may be desirable to select the image frame 910 that corresponds to the longer color quality bar with green color 912 as the optimal image frame.

Moreover, in accordance with yet another aspect of the present technique, a method for identifying an optimal image frame while imaging the femur of the fetus is presented. FIG. 10 is a diagrammatical representation 1000 of an image frame 1002 acquired while imaging a femur of the fetus. It may be noted while imaging the femur in the fetus, it may be desirable to identify one or more landmarks, such as, but not limited to sharp corners of a femur shaft 1004 and a surface 1006 that is adjacent to the femur shaft 1004. In one example, the adjacent surface 1006 may include the thigh skin.

Referring now to FIG. 11, a diagrammatical representation 1100 of a method for identifying an optimal image frame while imaging the fetal femur is depicted. The method starts at step 1102, where an image frame 1104 representative of the femur shaft 1106 of the fetus may be received. Reference numeral 1108 may be representative of the thigh skin that is disposed adjacent to the femur shaft 1106. Furthermore, at step 1102, presence of the femur shaft 1104 may be verified. In one embodiment, the presence of the femur shaft 1106 in the current image frame 1104 may be detected by verifying if the fetal femur 1106 is disposed such that the fetal femur 1106 is substantially horizontal with a tolerance of about 30 degrees.

As previously noted, for imaging the fetal femur it is desirable to identify an image frame that includes the thigh skin 1108, a visible sharp edge at least at one of the ends of the femur shaft 1106, and a femur shaft that is substantially horizontal. In accordance with aspects of the present technique, the method for identifying the optimal image frame corresponding to the fetal femur may include determining a first score corresponding to the sharpness of at least one edge of the femur shaft 1106 and a second score corresponding the thigh skin 1108 and generating a composite quality metric based on the first and second scores.

To that end, once the presence of the femur shaft 1106 is verified, it may be desirable to determine sharpness of at least one corner or extremity of the femur shaft 1106. Accordingly, at step 1110, one or more corners or extremities 1112, 1114 of the femur shaft 1106 may be localized. Furthermore, pixels corresponding to the localized corners or extremities may be clustered.

Subsequently, templates for the corners of the femur shaft 1106 may be obtained. Furthermore, the templates may be convolved with the identified corners 1112, 1114 to generate a first score 1116 corresponding to the corner sharpness of the femur shaft 1106. In one example, the current image frame may be multiplied with the template and all the pixel values may be added to generate the score for corner sharpness.

Moreover, the presence of a surface adjacent to the femur shaft 1106 may be verified. In one example, the adjacent surface may include the thigh skin 1108. Accordingly, at step 1118, the image frame 1104 may be processed to verify the presence of the thigh skin 1108. According to aspects of the present technique, an edge based template may be employed to aid in identifying/verifying the presence of the thigh skin 1108. In one embodiment, the edge based template may be based on the Active Basis technique. Subsequently, current image frame 1104 may be processed via/compared with the edge based template to generate a second score 1120 that is representative of the thigh skin visibility in the image frame 1104. In accordance with further aspects of the present technique, the first score 1116 and the second score 1120 may be combined to generate a composite quality metric 1122 that is representative of the quality of the current image frame 1104 while imaging the fetal femur.

As described hereinabove, the method for identifying an optimal image frame while imaging a fetal femur entails computation of a composite score based on the first and second scores. Alternatively, in certain embodiments, the image frame 1104 may be processed to verify the presence of the femur shaft 1106. Also, the orientation of the femur shaft 1106 may be determined. Subsequently, presence of a surface adjacent to the femur shaft, for example, the thigh skin 1108 may be verified. The image frames that include both the femur shaft 1106 and the thigh skin 1108 may identified. Following the identification of the desired image frames, the image frames may be processed to localize the extremities of the femur shaft 1106. Furthermore, pixels corresponding to the localized extremities may be clustered. In addition, the current image frame may be convolved with a template to generate a quality metric or score for that image frame. Also, an indicator representative of the quality metric may be generated and communicated as feedback to aid in the selection of the optimal image frame.

Here again, an indicator that is representative of the composite quality metric may be generated and communicated to the system 100 or the clinician to aid in selecting the optimal image frame. FIG. 12 is a diagrammatical representation 1200 of an output of the method for identifying an optimal image frame corresponding to the fetal femur. FIG. 12(*a*) is representative of a first image frame 1202 of the fetal femur. Also, in this example, an indicator representative of a quality of the first image frame 1202 is represented in the form of a quality bar 1204 that is superimposed on the first image frame 1202. Moreover, in FIG. 12(*b*), a second image frame 1206 of the fetal femur is represented. Also, an indicator corresponding to the quality metric of the second image frame 1206 is represented in the form of a quality bar 1208 that is superimposed on the second image frame 1206. In this example, the quality bars 1204, 1208 have a horizontal orientation and are superimposed along a lower border of the image frames 1202, 1206. However, the quality bar may be superimposed at other convenient locations. Accordingly, based on the feedback provided by the indicators 1204, 1208, the clinician or the system 100 may decide if the optimal image frame and been identified or if it is desirable to acquire more image frames of the fetal femur, thereby enhancing the imaging workflow by reducing scan time.

In the examples of FIGS. 12(*a*) and 12(*b*), the quality bar may be a color quality bar. One or more colors may be used in the quality bar to represent the quality of the image frame. By way of example, the quality bar 1204 of FIG. 12(*a*) may be a smaller red bar, while the quality bar 1208 of FIG. 12(*b*) may be a longer bar with a green color. Accordingly, it may be desirable to select the image frame 1206 that corresponds to the longer color quality bar with green color 1208 as the optimal image frame.

As previously noted with reference to FIG. 1, the medical imaging system 106 may include an ultrasound imaging system. FIG. 13 is a block diagram of an embodiment of an ultrasound imaging system 1300 depicted in FIG. 1. The ultrasound system 1300 includes an acquisition subsystem, such as the acquisition subsystem 108 of FIG. 1 and a processing subsystem, such as the processing subsystem 110 of FIG. 1. The acquisition subsystem 108 may include a transducer assembly 1306. In addition, the acquisition subsystem 108 includes transmit/receive switching circuitry 1308, a transmitter 1310, a receiver 1312, and a beamformer 1314. It may be noted that in certain embodiments, the transducer assembly 1306 is disposed in the probe 104 (see FIG. 1). Also, in certain embodiments, the transducer assembly 1306 may include a plurality of transducer elements (not shown) arranged in a spaced relationship to form a transducer array, such as a one-dimensional or two-dimensional transducer array, for example. Additionally, the transducer assembly 1306 may include an interconnect structure (not shown) configured to facilitate operatively coupling the transducer array to an external device (not shown), such as, but not limited to, a cable assembly or associated electronics. In the illustrated embodiment, the interconnect structure may be configured to couple the transducer array to the T/R switching circuitry 1308.

The processing subsystem 110 includes a control processor 1316, a demodulator 1318, an imaging mode processor 1320, a scan converter 1322 and a display processor 1324. The display processor 1324 is further coupled to a display monitor 1336, such as the display 116 (see FIG. 1), for displaying images. User interface 1338, such as the user interface area 118 (see FIG. 1), interacts with the control processor 1316 and the display monitor 1336. The control processor 1316 may also be coupled to a remote connectivity subsystem 1326 including a remote connectivity interface 1328 and a web server 1330. The processing subsystem 110 may be further coupled to a data repository 1332, such as the data repository 114 of FIG. 1, configured to receive and/or store ultrasound image data. The data repository 1332 interacts with an imaging workstation 1334.

The aforementioned components may be dedicated hardware elements such as circuit boards with digital signal processors or may be software running on a general-purpose computer or processor such as a commercial, off-the-shelf personal computer (PC). The various components may be combined or separated according to various embodiments of the invention. Thus, those skilled in the art will appreciate that the present ultrasound imaging system 1300 is provided by way of example, and the present techniques are in no way limited by the specific system configuration.

In the acquisition subsystem 108, the transducer assembly 1306 is in contact with the patient 102 (see 1306 FIG. 1). The transducer assembly 1306 is coupled to the transmit/receive (T/R) switching circuitry 1308. Also, the T/R switching circuitry 1308 is in operative association with an output of transmitter 1310 and an input of the receiver 1312. The output of the receiver 1312 is an input to the beamformer 1314. In addition, the beamformer 1314 is further coupled to the input of the transmitter 1310 and to the input of the demodulator 1318. The beamformer 1314 is also operatively coupled to the control processor 1316 as shown in FIG. 13.

In the processing subsystem 110, the output of demodulator 1318 is in operative association with an input of the imaging mode processor 1320. Additionally, the control processor 1316 interfaces with the imaging mode processor 1320, the scan converter 1322 and the display processor 1324. An output of imaging mode processor 1320 is coupled to an input of scan converter 1322. Also, an output of the scan converter 1322 is operatively coupled to an input of the display processor 1324. The output of display processor 1324 is coupled to the monitor 1336.

Furthermore, the foregoing examples, demonstrations, and process steps such as those that may be performed by the system may be implemented by suitable code on a processor-based system, such as a general-purpose or special-purpose computer. It should also be noted that different implementations of the present technique may perform some or all of the steps described herein in different orders or substantially concurrently, that is, in parallel. Furthermore, the functions may be implemented in a variety of programming languages, including but not limited to C++ or Java. Such code may be stored or adapted for storage on one or more tangible, machine readable media, such as on data repository chips, local or remote hard disks, optical disks (that is, CDs or DVDs), memory or other media, which may be accessed by a processor-based system to execute the stored code. Note that the tangible media may comprise paper or another suitable medium upon which the instructions are printed. For instance, the instructions may be electronically captured via optical scanning of the paper or other medium, then compiled, interpreted or otherwise processed in a suitable manner if necessary, and then stored in the data repository or memory.

The various systems and methods for automated identification of an optimal image frame for ultrasound imaging described hereinabove provides a framework for robust determination of an optimal image frame for imaging a desired anatomical region of interest, such as the heart, the fetal head, and/or the fetal femur. Moreover, the various systems and methods are automated, thereby circumventing the need for manual intervention. Consequently, dependency on highly trained professionals is reduced. In addition, the scan time may be dramatically minimized when compared to manual image acquisition and measurement, thereby increasing the throughput. Both image acquisition and measurement phases are tied together into one automated process. Moreover, these methods and systems may be configured to process image frames acquired from low-cost imaging systems, thereby addressing the needs of the rural markets. By way of example, for rural setups with high volumes of fetal scanning, these systems and methods aid in decreasing the net scan time, thereby enhancing handling of higher volumes.

Furthermore, the visual and/or audio indicators introduced into the current workflow of ultrasound scanning enhance ease of use of the system by a visual and/or audio cue as a quality indicator. Less experienced clinicians greatly benefit from these features since the system provides feedback corresponding to the quality of the acquisition in real-time. In addition, the more experienced clinicians may use these indicators as a way to reconfirm their findings. Moreover, for clinicians with heavy workloads, the increased automation and assistance provided by the systems enables the clinicians to perform a greater volume of fetal scanning. Also, the clinical workflow is enhanced due to the reduced number of button clicks. The feedback provided may also be used to train new users and assist less skilled users in their practice.

While only certain features of the disclosure have been illustrated and described herein, many modifications and changes will occur to those skilled in the art. It is, therefore, to be understood that the appended claims are intended to cover all such modifications and changes as fall within the true spirit of the disclosure.

The invention claimed is:

1. A method for identifying an optimal image frame, comprising:
receiving, by a rating platform, a selection of an anatomical region of interest in an object of interest;
obtaining, by an acquisition subsystem, a plurality of image frames corresponding to the selected anatomical region of interest;
enhancing, by the rating platform, a contrast of one or more features of interest in the plurality of image frames;
computing, by the rating platform, a quality metric representative of a quality of the plurality of image frames by comparing the plurality of image frames with a determined model, wherein the determined model comprises an atlas corresponding to the one or more features of interest in the plurality of image frames, and wherein the atlas is generated based on a shape-based averaging;
determining, by the rating platform, a real-time indicator corresponding to the plurality of acquired image frames, wherein the real-time indicator is representative of a quality of an image frame; and
communicating, by the rating platform, the real-time indicator to aid in selecting an optimal image frame.

2. The method of claim 1, wherein the object of interest comprises a patient, a fetus, or a test object.

3. The method of claim 1, further comprising identifying a cluster of neighboring image frames of the image frame that comprises a feature of interest based on the quality metric.

4. The method of claim 1, wherein the anatomical region of interest comprises a heart, a fetal head, a fetal femur, or combinations thereof.

5. The method of claim 1, further comprising:
identifying presence of a fetal head in the plurality of image frames to form a first subset of image frames, wherein the image frames in the first subset of image frames comprise the fetal head; and
identifying presence of a midline falx in the first subset of image frames to form a second subset of image frames, wherein the image frames in the second subset of image frames comprise at least the midline falx.

6. The method of claim 5, further comprising identifying presence of a paired thalami and a cavum septum pellucidum in the second subset of image frames to form a third subset of image frames, wherein the image frames in the third subset of image frames comprise at least the paired thalami and the cavum septum pellucidum.

7. The method of claim 6, wherein identifying the presence of the paired thalami and the cavum septum pellucidum in the second subset of image frames to form a third subset of image frames comprises comparing the image frames in the second subset with a determined model, and wherein the determined model is representative of an average of shapes, appearances, or combinations thereof of the anatomical region of interest.

8. The method of claim 7, further comprising determining a closeness of fit based on the determined model to generate the quality metric.

9. The method of claim 1, wherein the plurality of image frames comprises a cardiac image frame, and wherein the cardiac image frame comprises a Parasternal Long Axis (PLAX) view image frame.

10. The method of claim 9, further comprising filtering the cardiac image frame with enhanced contrast to generate a binary image comprising the one or more features of interest.

11. The method of claim 10, wherein comparing the plurality of image frames comprises comparing the binary image with the determined model to determine a closeness of fit of the binary image to the determined model to generate the quality metric.

12. The method of claim 10, wherein comparing the binary image with the atlas is based on a Generalized Hough Transform.

13. The method of claim 10, wherein comparing the binary image comprises determining a most probable location of the atlas on the binary image.

14. The method of claim 13, further comprising determining a PLAX quality metric based on a closeness of fit of the atlas to the binary image.

15. The method of claim 1, wherein communicating the real-time indicator to the clinician comprises visualizing the real-time indicator on a display, playing an audio-indicator of the real-time indicator, or a combination thereof.

16. A computer-readable non-transitory media storing computer executable code to perform the method of:
- receiving a selection of an anatomical region of interest in an object of interest;
- obtaining a plurality of image frames corresponding to the selected anatomical region of interest;
- enhancing a contrast of one or more features of interest in the plurality of image frames;
- computing a quality metric representative of a quality of the plurality of image frames by comparing the plurality of image frames with a determined model, wherein the determined model comprises an atlas corresponding to the one or more features of interest in the plurality of image frames, and wherein the atlas is generated based on a shape-based averaging;
- determining a real-time indicator corresponding to the plurality of acquired image frames, wherein the real-time indicator is representative of a quality of an image frame; and
- communicating the real-time indicator to aid in selecting an optimal image frame.

17. An imaging system, the system comprising:
- an acquisition subsystem configured to obtain a plurality of image frames corresponding to a region of interest in an object of interest;
- a processing subsystem in operative association with the acquisition subsystem and comprising a rating platform, wherein the rating platform comprises:
  - a feature extraction module configured to extract one or more features of interest from the plurality of image frames;
  - a quality metric generator module configured to generate a quality metric corresponding to one or more image frames in the plurality of image frames by comparing the plurality of image frames with a determined model wherein the determined model comprises an atlas corresponding to one or more features of interest in the plurality of image frames, and wherein the atlas is generated based on a shape-based averaging;
  - an image frame selector module configured to select one or more image frames based on the quality metric; and
  - a feedback module configured to generate and communicate in real-time an indicator representative of the quality metric.

18. The system of claim 17, wherein the system comprises an ultrasound imaging system, a contrast enhanced ultrasound imaging system, an optical imaging system, an X-ray imaging system, a computed tomography imaging system, a magnetic resonance imaging system, a computed tomography imaging system, a positron emission tomography imaging system, or combinations thereof.

19. A method for identifying an optimal image frame, comprising:
- receiving, by a rating platform, a selection of an anatomical region of interest in an object of interest;
- obtaining, by an acquisition subsystem, a plurality of image frames corresponding to the selected anatomical region of interest;
- processing, by the rating platform, the plurality of images frames, wherein processing the plurality of image frames comprises:
  - identifying a femur shaft using the plurality of image frames;
  - determining an orientation of the femur shaft;
  - detecting an adjacent surface of the femur shaft based on an edge based template;
  - localizing extremities of the femur shaft;
  - clustering pixels corresponding to the localized extremities;
  - convolving the plurality of image frames with corner features of a template to generate a metric for corner sharpness;
- determining, by the rating platform, a real-time indicator corresponding to the plurality of acquired image frames, wherein the real-time indicator is representative of quality of an image frame; and
- communicating, by the rating platform, the real-time indicator to aid in selecting an optimal image frame.

20. The method of claim 19, further comprising generating a quality metric representative of a quality of the image frame.

* * * * *